United States Patent
Dickson

(10) Patent No.: US 9,649,260 B2
(45) Date of Patent: May 16, 2017

(54) NIPPLE SHIELD

(71) Applicant: Magdalena Dickson, Bradenton, FL (US)

(72) Inventor: Magdalena Dickson, Bradenton, FL (US)

(*) Notice: Subject to any disclaimer, the term of this patent is extended or adjusted under 35 U.S.C. 154(b) by 0 days.

(21) Appl. No.: 14/658,231

(22) Filed: Mar. 15, 2015

(65) Prior Publication Data

US 2016/0262946 A1    Sep. 15, 2016

(51) Int. Cl.
*A61F 13/00* (2006.01)
*A61J 13/00* (2006.01)
*A61B 90/00* (2016.01)
*A61B 17/00* (2006.01)

(52) U.S. Cl.
CPC .............. *A61J 13/00* (2013.01); *A61B 90/00* (2016.02); *A61B 90/08* (2016.02); *A61B 2017/00796* (2013.01)

(58) Field of Classification Search
CPC .................... A61F 13/14; A61F 13/145; A61F 2013/00093; A61F 2013/00357; A61J 13/00
USPC ......................................................... 128/888
See application file for complete search history.

(56) References Cited

U.S. PATENT DOCUMENTS

| 4,754,750 | A | * | 7/1988 | Imonti | A61F 15/008 128/888 |
| 4,790,309 | A | * | 12/1988 | Becker | A61F 2/12 606/1 |
| 4,870,977 | A | * | 10/1989 | Imonti | A61F 15/008 128/888 |
| 5,772,654 | A | * | 6/1998 | Leyva | A61B 17/3403 128/897 |
| 5,782,672 | A | * | 7/1998 | Woodley | A41C 3/065 2/267 |
| 8,808,262 | B2 | * | 8/2014 | Krasikoff | A61F 13/14 604/385.07 |
| 2014/0200529 | A1 | * | 7/2014 | Hyde-Edwards | A61F 13/145 604/304 |
| 2014/0305446 | A1 | * | 10/2014 | Raniere | A61F 13/14 128/890 |

FOREIGN PATENT DOCUMENTS

WO    WO 8806877 A1 * 9/1988 .......... A61F 15/008

* cited by examiner

*Primary Examiner* — Kristen Matter
(74) *Attorney, Agent, or Firm* — Knox Patents; Kenneth C. Spafford

(57) ABSTRACT

A shield for a post-operative reconstructed nipple is disclosed. The shield includes a vertical shield portion and a flat base with rounded corners and symmetric suture holes. The shield may be made of polyethylene or other semi-rigid material. The shield is sutured to a patient's skin through the suture holes, with the shield base imposed on a dressing such as iodiform gauze that is in contact with the patient's skin.

16 Claims, 4 Drawing Sheets

NIPPLE SHIELD

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND

1. Field of Invention

This disclosure pertains to shielding a post-surgical reconstructed nipple. More particularly, this invention pertains to an open-end nipple shield that may be easily sutured to a patient's skin surrounding a reconstructed nipple.

2. Description of the Related Art

The current preferred method for nipple reconstruction is to make small incisions on the skin of a breast that has been reconstructed either by autologous reconstruction or breast implant. The cut tissue is then elevated, and formed and shaped into a living tissue projection that mimics the natural nipple. A common incision/elevation method is the "star" dermal flap pattern, which comprises elevation of the skin flaps of the cut "star" pattern and wrapping the star "wings" around each other.

Nipple construction is the last stage of breast reconstruction and is performed when the surgeon is confident that the prior reconstruction stages have sufficiently healed and that both the contour and shape of the reconstructed breast have achieved their final acceptable symmetry.

The technical challenges of nipple reconstruction include maintaining a desirable nipple projection and leaving an inconspicuous scar. Tissue heals in response to the forces that are placed upon it and the position the tissue is in. Thus, during the post-operative stage the protection of a newly created nipple from outside forces is crucial. A newly constructed nipple is extremely sensitive to shearing and pressure forces, which may result in flattening of a nipple.

Typical prior art for shielding nipples may be found in, for example, U.S. Pat. No. 4,870,977 by Imonti (hereinafter "Imonti"), which discloses a cone-shaped nipple protector member having an outwardly-disposed flange. More recent art is found in U.S. Pat. No. 7,938,122 by Clark (hereinafter "Clark"), which discloses a nipple guard with a hollow core component, padding, and adhesive tape.

Both Imonti and Clark's devices may be appropriate for protecting a post-operative nipple under certain circumstances but do not fully address many of the collateral concerns related to the nipple healing process. For example, the earlier art by Imonti does not allow cleansing and proper medication ointment application without removal of the protector, and the slope of Imonti's cone-shaped nipple guards prevents effective cleaning by making it more difficult to insert a cleaning implement into the area around the nipple. As another example, both of the cited prior arts ordinarily use anchoring devices such as tape, which may produce allergic reactions in a patient and not adhere to skin correctly. Moreover, the devices taught by Imonti and Clark cover more skin tissue than may be necessary, thereby preventing proper air circulation on the tissue and creating constant moisture around the wound areas. In addition, Clark's device requires that the guard be changed "one to two times per day for up to sixteen weeks or longer," rather than use one guard that may be used for the entire recovery period. See Clark, Col. 8, 1. 48-50. Requiring so many changes will either reduce average patient compliance from missed appointments, or increase the likelihood of patient error if the patient is the one responsible for changing the guard.

BRIEF SUMMARY

According to one embodiment of the present invention, a nipple shield 100 is provided. Said embodiment includes a hexagonal base with rounded corners, a cylinder, and at least four apertures in said base.

It is an object of the present disclosure to provide a nipple shield that will allow a post-operation reconstructed nipple to heal properly.

It is another object of the present disclosure to provide a nipple shield that is easy to clean.

It is another object of the present disclosure to provide a nipple shield that allows the patient to take a shower the first day after surgery.

It is another object of the present invention to provide a nipple shield that allows the protected wound to dry properly.

It is another object of the present disclosure to provide a nipple shield that allows easy access and drying, cleaning, and ointment application on the reconstructed nipple and surrounding area without requiring removal of the nipple shield.

It is another object of the present invention to provide a nipple shield that does not require removal or replacement during its use.

It is another object of the present invention to provide a nipple shield made of strong durable material that may be affixed firmly in a single position and not subject to dislodging, torquing, rotating or shifting from external jostling.

It is another object of the present disclosure to provide a nipple shield that may be affixed easily to a patient.

It is another object of the present disclosure to provide a nipple shield that may be removed easily from a patient.

It is another object of the present disclosure to provide a cost-effective nipple shield.

It is another object of the present disclosure to provide a nipple shield that does not require tape to affix the shield to the patient's skin.

It is another object of the present disclosure to provide a nipple shield that covers a minimal amount of skin tissue.

It is another object of the present disclosure to provide a nipple shield that properly protects the post-operation nipple from flattening.

It is another object of the present disclosure to provide a nipple shield that improves patient compliance and reduces patient error by requiring less changing of the shield.

As used herein, positional terms such as "top", "bottom", "right", "left", "front", and "back" are relative within the disclosed drawings as labeled, and not intended to be absolute, and are only meant to provide a frame of reference for the displayed embodiment or embodiments rather than how the embodiments may be positioned when in use. By way of example, left tab 120 and right tab 122 may in fact be positioned such that they define a patient's sagittal plane (i.e., a vertically for a standing patient) rather than the patient's transverse plane.

BRIEF DESCRIPTION OF THE SEVERAL VIEWS OF THE DRAWINGS

The above-mentioned features will become more clearly understood from the following detailed description read together with the drawings in which.

DETAILED DESCRIPTION

Figure 1:
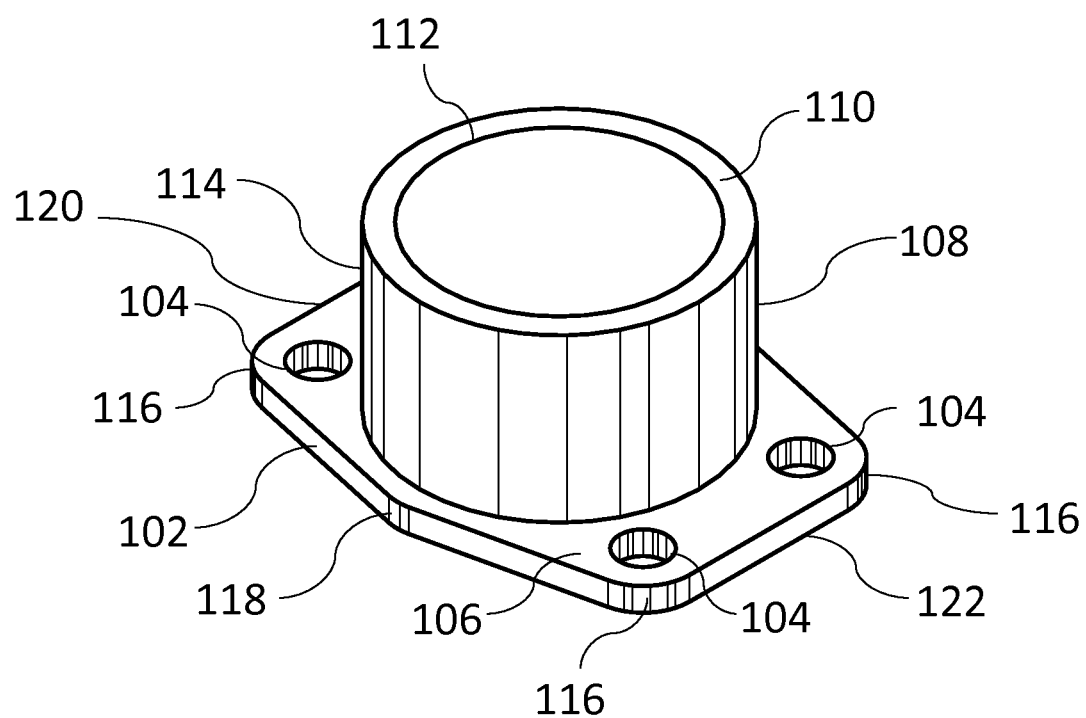
FIG. 1 is a top perspective view of an embodiment.

The apparatus for shielding post-operative nipple reconstruction is disclosed. The nipple shield is generally indicated as 100.

In ordinary circumstances the shield should be contained in packaging that allows the shield to remain sterile prior to use. The shield is typically meant for use on a single patient over a period of days or weeks.

In this embodiment, the nipple shield 100 is be made of one single molded piece or a combination fused cylinder 108 and base/flange 102 that include a left and right tab 120, 122. In this embodiment, the shield material is homogenous and consists of, for example, a plastic similar to the types of polyethylene plastics found in syringes. The thickness of both cylinder 108 and base 102 should be sufficient such that both cylinder 108 and base 102 are essentially rigid and inflexible, i.e., neither base bottom 302 nor cylinder 108 is subject to bending or misshaping when sutured to a patient. In this embodiment, base bottom 302 is flat rather than dome-shaped, thereby avoiding the base edges pressing into the patient's skin or incisions, and increasing stability.

Cylinder inner circumference 112 is not sloped but rather uniformly perpendicular with base 102, and cylinder inner circumference 112 has a diameter that is at least large enough such that cylinder 108 encircles and does not touch the reconstructed nipple. The height of cylinder 108 should be such that cylinder top 110 is higher than the top of the reconstructed nipple that the shield is protecting.

Figure 2:
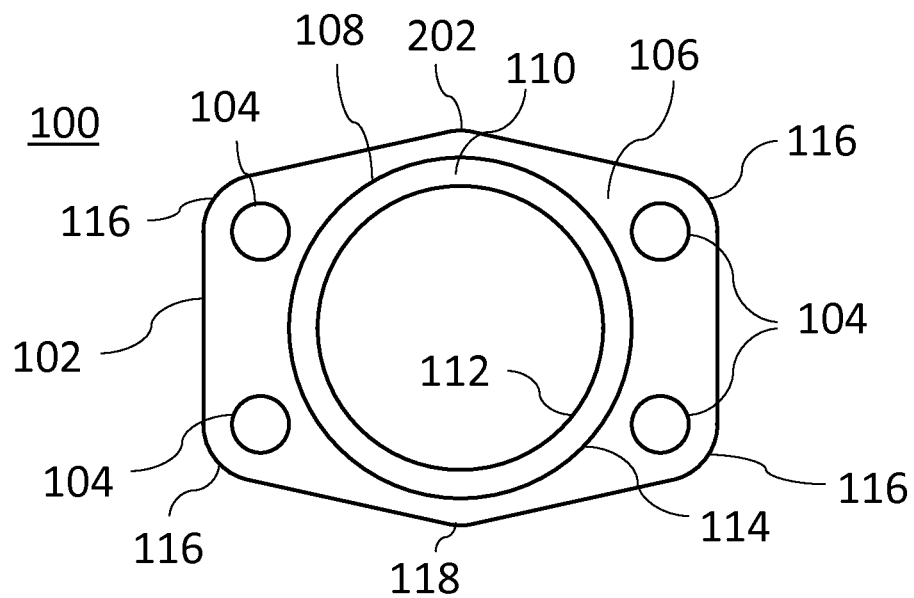
FIG. 2 is a top view of the embodiment of FIG. 1.
Figure 3:
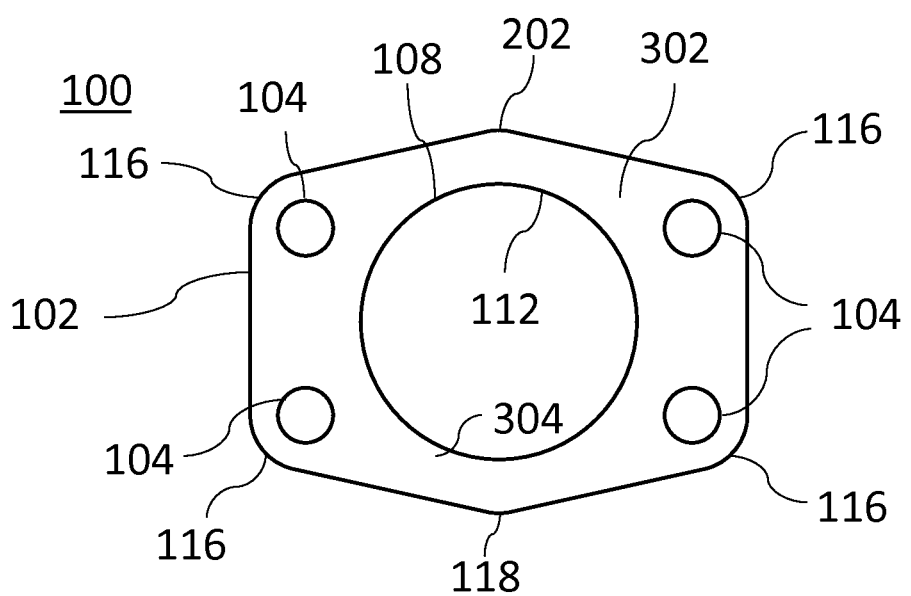
FIG. 3 is a bottom view of the embodiment of FIG. 1.
Figure 4:
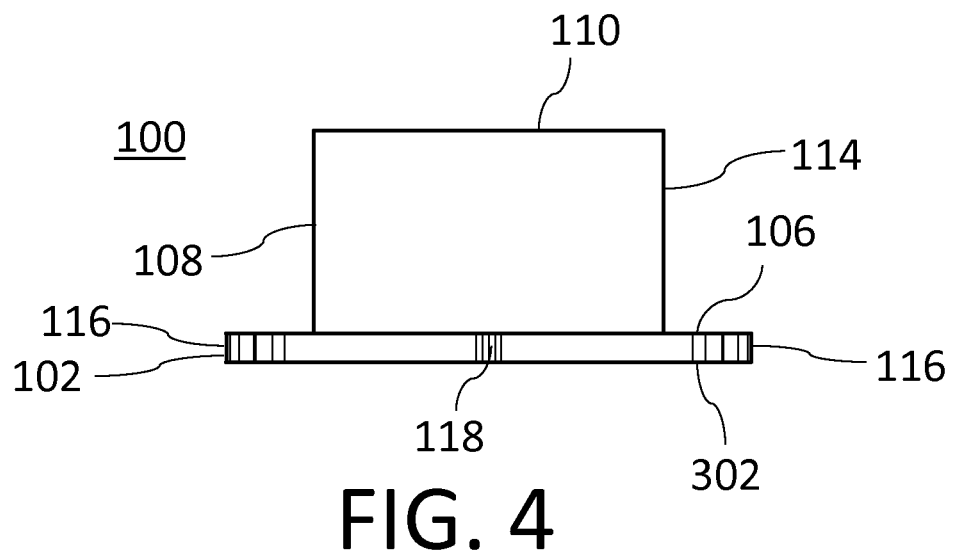
FIG. 4 is a front view of the embodiment of FIG. 1.
Figure 5:
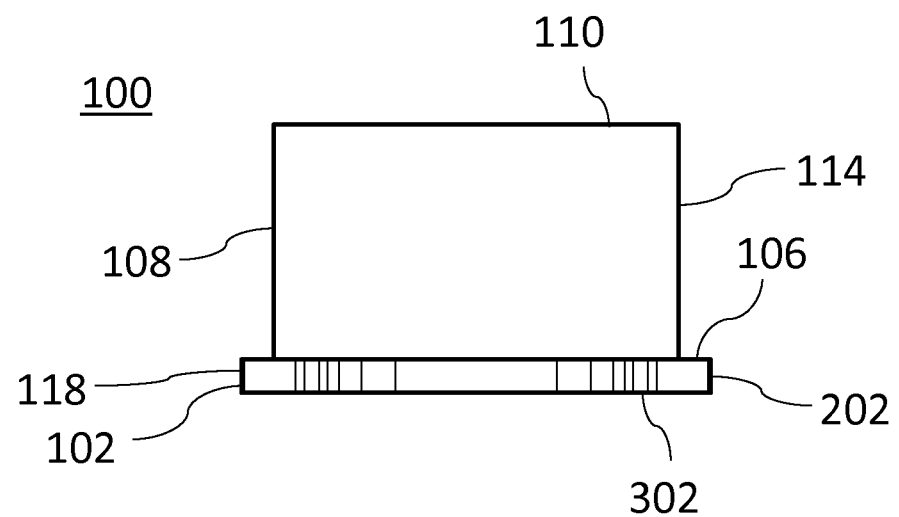
FIG. 5 is a side view of the embodiment of FIG. 1.
Figure 6A:
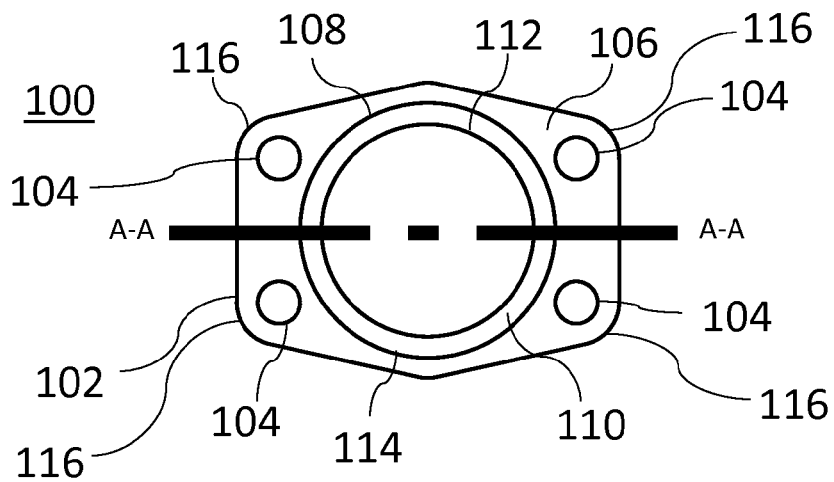
FIG. 6A displays a top view of the embodiment of FIG. 1, with line A-A showing the cross-section cut location of FIGS. 6B and 6C.
Figure 6B:
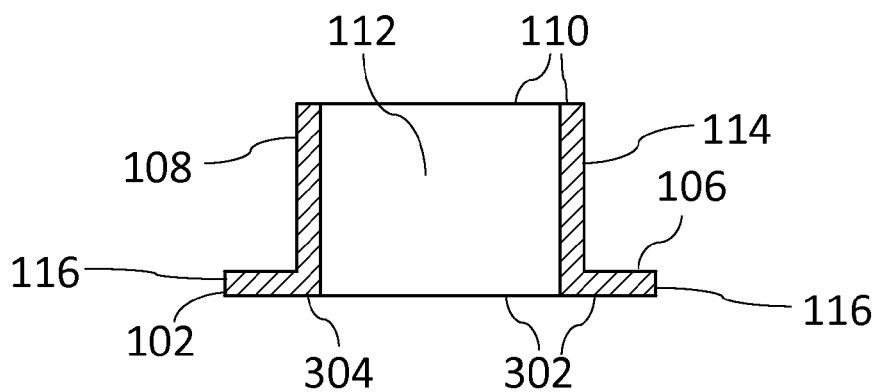
FIG. 6B is a side cross-section view of the embodiment of FIG. 1.
Figure 6C:
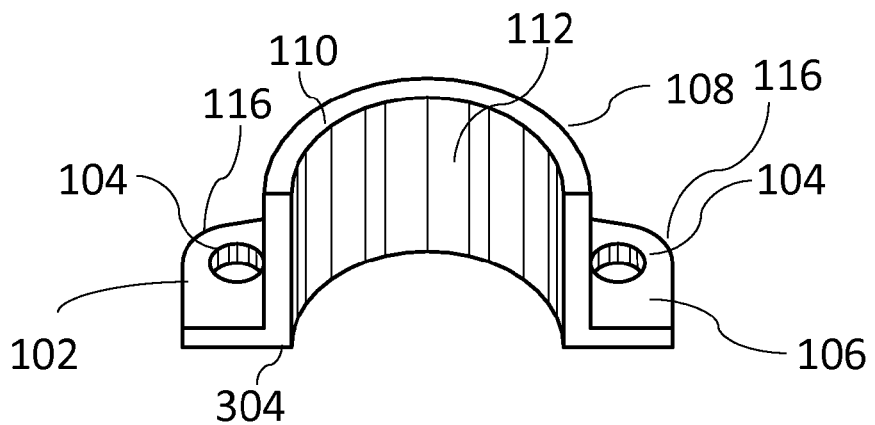
FIG. 6C is a side perspective cross-section view of the embodiment of FIG. 1.

As shown in FIG. 2, this shield 100 embodiment has both front-to-back and left-to-right reflection symmetry in order to allow a surgeon to affix the shield to a patient without having to consider or remember extra positioning requirements. Suture holes 104 are aligned in this embodiment such that the centers of the holes collectively define the corners of a rectangle.

Base 102 includes at least four suture holes 104 that pass orthogonally from base top 106 to base bottom 302 and that are of sufficient diameter relative to base thickness such that a desired curved suture needle (for example, a standard size ⅜ suture needle) passes through a suture hole without difficulty. In this embodiment, base top and bottom 106, 302 are parallel.

Each of the four suture holes 104 is between a corresponding rounded corner 116 and cylinder 108. Two holes are on each tab 120, 122.

In order to minimize the skin area covered by the embodiment during use, base 102 is sufficiently narrow such that cylinder outer circumference 114 is completely interposed between left and right side suture holes 104, and completely interposed between right and left side and rounded corners 116. Front and rear rounded corners 118, 202 are located on opposite sides of cylinder 108 and each are a minimal distance from cylinder 108 such that suture holes 104 would not fit between cylinder 108 and rounded corners 118, 202. There is, however, enough distance between cylinder 108 and rounded corners 118, 202 to allow for structural integrity of the device and allow for a flat surface such that cylinder bottom 304 alone does not press into the patient's skin.

In an exemplary protoctol, a surgeon uses the shield 100 immediately following a surgical procedure. The surgeon applies, for example, an iodiform gauze or other thin dressing type of choice on the skin around the nipple, and then places the shield 100 on the gauze such that the incisions on the sides of the newly formed nipple do not directly touch the shield.

A 2-inch square iodiform gauze, for example, is fitted directly between the base 102 and the patient's incisions, i.e., the base 102 is imposed on the iodiform gauze; however, each surgeon has his or her own style of wound dressing and may use different dressing, other dressing patterns, or no dressing at all.

The surgeon then uses, for example, a ⅜ suture needle to suture the shield 100 to the patient's skin through the suture holes 104. The sutures should be short and binding enough so that the shield 100 cannot contact the reconstructed nipple even when lateral or torque forces are exerted against the cylinder top 110. However, the sutures should not be so tight as to prevent insertion of some small object, e.g., a cleaning device, between the shield 100 and skin if the skin near the shield were gently depressed with, for example, a finger.

In this embodiment affixing the nipple shield is performed as outpatient surgery. The patient has the option of showering the night of surgery or the following morning. Ointment is applied to the reconstructed nipple without removing or unsuturing the shield 100.

From the foregoing description, it will be recognized by those skilled in the art that a simple, sturdy disposable nipple shield has been provided.

While the present inventions have been illustrated by embodiment and while the illustrative embodiment has been described, it is not the intention of the applicant to restrict or in any way limit the scope of the appended claims to such detail. Additional advantages and modifications will readily appear to those skilled in the art. The inventions in their broader aspects are therefore not limited to the specific details, representative apparatus and methods, and illustrative examples shown and described. Accordingly, departures may be made from such details without departing from the spirit or scope of applicant's general inventive concepts.

What is claimed is:

1. A method for shielding and treating a post-operative nipple on a patient, comprising:
    (A) providing a nipple shield including: a cylinder with a top end and a bottom end, wherein said cylinder is open on both ends and sized to encase a patient's nipple; a flange located at said cylinder bottom end, wherein said flange includes four suture holes and is perpendicular to said cylinder; wherein said four suture holes define the corners of a rectangle whose short sides are shorter than the cylinder outer diameter and whose long sides are longer that the cylinder outer diameter;
    (B) suturing said nipple shield to the patient's skin through each of said suture holes, wherein said nipple shield is positioned such that said cylinder is surrounding but not touching the patient's post-operative reconstructed nipple.

2. The method of claim 1, wherein said suture holes are operable to allow a ⅜ suture needle to pass through each of said holes, and wherein said suturing is performed with a ⅜ suture needle.

3. The method of claim 1, wherein said shield is not unsutured from the patient's skin for at least a week.

4. The method of claim 3, further comprising the patient taking a full shower subsequent to, and on the same day of, the shield being sutured to the patient's skin.

5. The method of claim 1, further comprising verifying that the reconstructed nipple does not extend past the top end of the cylinder.

6. The method of claim 1, further comprising applying gauze around the reconstructed nipple such that said flange is at least partially imposed on said gauze.

7. The method of claim 1, wherein said suturing is sewn to allow for a cleaning device to be inserted between the shield and the patent's skin when the skin is gently depressed with a finger.

8. The method of claim 1 wherein said suturing is tightened such that said shield does not contact the patient's nipple when a lateral force is exerted against said cylinder top end.

9. The method of claim 1, further comprising a subsequent step of cleaning the nipple without removing the nipple shield.

10. The method of claim 1, further comprising applying ointment to the nipple without unsuturing said nipple shield.

11. A method for shielding and treating a post-operative nipple on a patient, comprising:

(A) positioning a nipple shield on [a] the patient such that the patient's nipple is surrounded by, but not touching, an open cylinder that is part of the nipple shield;

(B) placing onto the patient's skin a flange that is located on a bottom end of said cylinder and is perpendicular to the cylinder, such that a top end of said cylinder is higher than the patient's nipple; and (C) suturing said nipple shield to the patient's skin through four suture holes located on said flange, wherein said four suture holes define the corners of a rectangle whose short sides are shorter than the cylinder outer diameter and whose long sides are longer that the cylinder outer diameter.

12. The method of claim 11, further comprising the patient taking a full shower within 24 hours of said nipple shield being sutured to the patient's skin.

13. The method of claim 11, further comprising not removing the nipple shield from the patient for at least one week subsequent to suturing the nipple shield to the patient.

14. The method of claim 11, further comprising positioning a piece of gauze around the nipple and at least partially between said nipple shield and the patient's skin.

15. The method of claim 11, further comprising a subsequent step of cleaning the nipple without removing the nipple shield.

16. The method of claim 11, further comprising applying ointment to the nipple without unsuturing said nipple shield.

* * * * *